(12) United States Patent
Ferritto et al.

(10) Patent No.: US 8,278,288 B2
(45) Date of Patent: Oct. 2, 2012

(54) ORGANOSILOXANES CONTAINING ESTER DERIVATIVES OF ASCORBIC ACID

(75) Inventors: Michael Salvatore Ferritto, Midland, MI (US); Eric Jude Joffre, Midland, MI (US); Margo L. McIvor, Midland, MI (US); Michael Stephen Starch, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 309 days.

(21) Appl. No.: 12/680,407

(22) PCT Filed: Sep. 16, 2008

(86) PCT No.: PCT/US2008/076494
§ 371 (c)(1),
(2), (4) Date: Mar. 26, 2010

(87) PCT Pub. No.: WO2009/045709
PCT Pub. Date: Apr. 9, 2009

(65) Prior Publication Data
US 2010/0221201 A1   Sep. 2, 2010

Related U.S. Application Data

(60) Provisional application No. 60/975,863, filed on Sep. 28, 2007.

(51) Int. Cl.
*A01N 55/00* (2006.01)
*A01N 37/08* (2006.01)
*A01N 37/02* (2006.01)
*C07F 7/04* (2006.01)
*C07F 7/08* (2006.01)
*C07F 7/00* (2006.01)
*A61K 8/00* (2006.01)

(52) U.S. Cl. .......... 514/63; 514/530; 514/548; 514/552; 556/437; 556/457; 556/489; 556/482; 556/438; 556/456; 424/59

(58) Field of Classification Search .................. None
See application file for complete search history.

(56) References Cited

U.S. PATENT DOCUMENTS

| | | | |
|---|---|---|---|
| 4,939,128 A | 7/1990 | Kato et al. | |
| 4,999,437 A | 3/1991 | Dobler et al. | |
| 5,990,069 A | 11/1999 | Andre et al. | |
| 6,200,581 B1 | 3/2001 | Lin et al. | |
| 6,780,888 B1 | 8/2004 | Xu et al. | |
| 7,132,558 B1 | 11/2006 | O'Lenick, Jr. et al. | |
| 2008/0118454 A1 | 5/2008 | McAuliffe et al. | |

FOREIGN PATENT DOCUMENTS

| | | |
|---|---|---|
| WO | WO9618729 | 6/1996 |
| WO | WO0130784 | 5/2001 |
| WO | WO2004016625 | 2/2004 |
| WO | WO 2006/066227 A2 * | 6/2006 |
| WO | WO2006066227 | 6/2006 |

* cited by examiner

*Primary Examiner* — Richard Schnizer
*Assistant Examiner* — Alma Pipic
(74) *Attorney, Agent, or Firm* — Alan Zombeck

(57) ABSTRACT

Organosiloxanes containing ester derivatives of ascorbic acid are disclosed having the formula $(R_iSiO)_{11}R_{o-Ii})Si-X-A$ wherein R is an alkyl group containing 1 to 6 carbon atoms, n is 1 to 3 inclusive, X is a divalent organic linking group, A is an ester derivative of ascorbic acid. A method of making an organosiloxane containing ester derivatives of ascorbic acid and the products prepared according to the method are also taught. The compounds and compositions of the present disclosure are useful to affect tissue lightening when applied topically to keratinaceous tissue.

14 Claims, No Drawings

ORGANOSILOXANES CONTAINING ESTER DERIVATIVES OF ASCORBIC ACID

CROSS REFERENCE TO RELATED APPLICATIONS

This application is a U.S. national stage filing under 35 U.S.C. §371 of PCT Application No. PCT/US08/76494 filed on Sep. 1, 2008, currently pending, which claims the benefit of U.S. Provisional Patent Application No. 60/975,863 filed Sep. 28, 2007 under 35 U.S.C. §119(e). PCT Application No. PCT/US08/76494 and U.S. Provisional Patent Application No. 60/975,863 are hereby incorporated by reference.

TECHNICAL FIELD

This disclosure relates to organosiloxanes having the formula 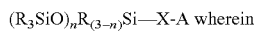 wherein R is an alkyl group containing 1 to 6 carbon atoms, n is 1 to 3 inclusive, X is a divalent organic linking group, and A is an ester derivative of ascorbic acid. This disclosure further relates to a method of making an organosiloxane containing ester derivatives of ascorbic acid and the products prepared according to the method. The compounds and compositions of the present disclosure are useful to affect tissue lightening when applied topically to keratinaceous tissue.

BACKGROUND

Ascorbic acid and related compounds are of known utility in skin-lightening and other technologies related to hyperpigmentation. Ascorbic acid formulations, however, are prone to oxidation and are easily destabilized. In addition, cosmetic or pharmacological compositions comprising these acids may damage tissue or irritate human skin on repeated topical applications due to lower pH of the formulations. Hence, ascorbic acid and other related compounds have been compounded with other hydrophobic materials to improve their stability and performance. Most recently, ester derivatives of ascorbic acid and 2-keto-acid saccharides have been disclosed in WO 2006/066227 wherein the ester is introduced by ester bond formation between at least one hydroxy-functionality on the ascorbic acid or 2-keto-acid saccharide and a carboxy-functional organosiloxane. The organosiloxane structures suggested in WO 2006/066227 are numerous. However, the working examples in WO 2006/066227 emphasized A-B-A structures based on a linear polydimethylsiloxane having end groups containing an ester linkage to ascorbic acid. While the examples in WO 2006/066227 demonstrated skin lightening effects and good formulation stabilities, they did not provide skin lightening effects equivalent or better than kojic acid. Kojic acid is known for its skin lightening capabilities and is often used as a benchmark for determining skin lightening performance. However, kojic acid's water solubility can limit its delivery and formulation latitude. Furthermore, the use of kojic acid in skin care formulation is questioned in some countries for safety reasons.

The present inventors have unexpectedly discovered certain short chain organosiloxanes containing ester derivatives of ascorbic acid provide enhanced skin lightening performance. In particular, these ascorbyl containing short chain organosiloxanes have skin lightening performance comparable to or better than kojic acid. Furthermore, the present ascorbyl containing short chain organosiloxanes are useful in many personal care formulations because of their compatibility with many organic oils and silicones.

SUMMARY

This disclosure relates to compounds having the formula $(R_3SiO)_n R_{(3-n)}Si$—X-A wherein R is an alkyl group containing 1 to 6 carbon atoms,
n is 1 to 3 inclusive,
X is a divalent organic linking group,
A is an ester derivative of ascorbic acid.

This disclosure further provides a method of making an organosiloxane containing ester derivatives of ascorbic acid and the products prepared according to the method, the method comprising:

I) providing a protected ascorbic acid by forming a protecting group from at least one hydroxy-functional group thereon;
II) mixing the protected ascorbic acid with a carboxy-functional organosiloxane having the formula $(R_3SiO)_n R_{(3-n)}Si$—X—C(O)OR$^1$
where R is an alkyl group containing 1 to 6 carbon atoms,
n is 1 to 3 inclusive, X is a divalent organic linking group,
R$^1$ is a hydrocarbyl containing 1 to 20 carbon atoms or hydrogen, to form a solution;
III) contacting the solution with a biocatalyst which is capable of catalyzing ester bond formation;
IV) optionally, removing the protecting group, and wherein the protecting group may comprise a functional group.

This disclosure further relates to compositions comprising the present organosiloxane compounds and a carrier fluid.

When the compounds and compositions of the present disclosure are applied topically to keratinaceous tissue, and in particular human skin, tissue lightening effects are effected.

This disclosure yet further relates to keratinaceous tissue lightening agent compositions comprising the compound and compositions described herein.

This disclosure yet further relates to personal care compositions containing the compounds and compositions described herein.

DETAILED DESCRIPTION

This disclosure relates to organosiloxane compounds having the formula

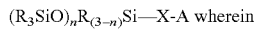 wherein

R is an alkyl group containing 1 to 6 carbon atoms,
n is 1 to 3 inclusive, alternatively n is 2.
X is a divalent organic linking group, and
A is an ester derivative of ascorbic acid, R may be any alkyl group containing 1 to 6 carbons such as methyl, ethyl, propyl, isopropyl, butyl, isobutyl, pentyl, or hexyl. Alternatively, R is methyl.

X is a divalent organic linking group. While X may be any organic linking group, typically X contains 1 to 30 carbon atoms. X may be a linear or branched $C_1$-$C_{30}$ alkylene chain. Thus X may be a divalent, aliphatic hydrocarbon group having 1-30 carbons, alternatively having 3-12 carbons, or alternatively having 10 carbons such as —$(CH_2)_{10}$—.

A is an ester derivative of ascorbic acid. The scope of the inventive compounds includes all ester derivatives of ascorbic acid and isoascorbic acid wherein the organosiloxane is covalently bound to the ascorbic, or isoascorbic via an ester bond. As used herein the term "ascorbic acid" includes ascorbic acid and its diastereoisomer, isoascorbic acid, unless specifically referred to as L-ascorbic acid or D-eiythorbic acid, and salts thereof. The fourth and fifth carbon atoms of an ascorbic acid molecule are chiral, leading to the existence of two enantiomeric isomers at each chiral center for a total of 4 diasteroisomers. One of the enantiomers of isoascorbic acid is also known as D-erythorbic acid. Due to its strong reducing properties, D-erythorbic acid has similar technological applications to L-ascorbic acid as a water-soluble antioxidant. "Ascorbic acid" also includes the derivatives of all distereoisomers, including those wherein one or more of the free hydroxy functional groups thereof are formed as esters, ethers, ketones, and so forth, and including those comprising groups intended to be protecting and/or functional groups.

In the $(R_3SiO)_n R_{(3-n)}Si$—X-A formula, A may have the following structure;

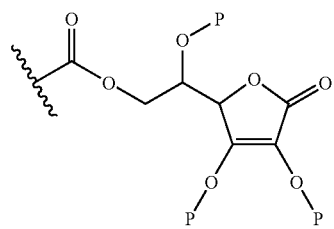

where each P is independently any protecting or functional group, a proton or a cation chosen from the alkali or alkaline earth metals. As used herein the term "protecting group" includes groups formed involving one or more of the free hydroxy functional groups of the ascorbic acid, and includes esters, ethers, ketones and so forth. In one embodiment, the process to form the ester derivative comprises "protecting" at least one of the hydroxyl groups of the ascorbic acid or derivatives thereof as esters (for example, as acetate esters) or ethers (for example, methyl ethers or), epoxys, or cyclic ketals. In a specific embodiment the ascorbic acid is protected at one or more hydroxyl sites by initial conversion to the cyclic ketal by the formation of 2,3-isopropylidene-ascorbic acid. Also as used herein the term "protecting" group may include a functional group, or added functionality may not relate to "protecting" at all. In one embodiment, the ascorbic acid comprises at least one hydroxy group which is functionalized or protected or both.

In another specific embodiment, the ascorbic acid is protected at one or more hydroxyl sites as esters (for example as O-carbonates, O-acetates, O-phosphates and the like). The latter may then be derivatized using biocatalyzed esterification methods described below ultimately to produce the structures of the present disclosure. In addition, the formation of mono and diphosphates of ascorbic acid are described thoroughly in the literature. For example, U.S. Pat. No. 4,939,128 to Kato et al., the contents of which are incorporated herein by reference, teaches the formation of phosphoric acid esters of ascorbic acid. Similarly, U.S. Pat. No. 4,999,437 to Dobler et al., the contents of which are also fully incorporated herein by reference, describes the preparation of ascorbic acid 2-phosphate. In another specific embodiment the ascorbic acid is protected at the hydroxyls by formation of ethers, and in a very specific embodiment the protecting moiety is a trimethylsilyl ether. Any of these known ascorbic acid derivatives can be used within the scope of the present invention.

In one very specific embodiment, the organosiloxane compound has the formula;

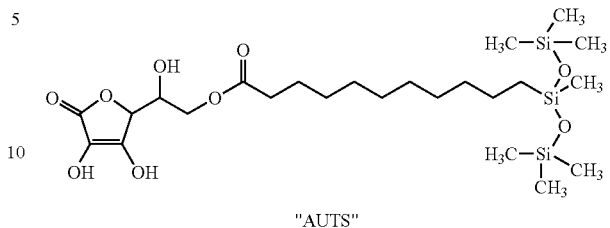

"AUTS"

referred herein as "AUTS".

The process or method of making the organosiloxanes containing ester derivatives of ascorbic acid as described above may vary. Alternatively, they may be prepared by methods as described herein. Thus, the present disclosure further provides a method of making organosiloxanes containing ester derivatives of ascorbic acid comprising:

I) providing a protected ascorbic acid by forming a protecting group from at least one hydroxy-functional group thereon;

II) mixing the protected ascorbic acid with a carboxy-functional organosiloxane having the formula $(R_3SiO)_n R_{(3-n)}Si$—X—C(O)OR$^1$ where R, n and X are the same as described above, and R$^1$ is a hydrocarbyl containing 1 to 20 carbon atoms or hydrogen, to form a solution;

III) contacting the solution with a biocatalyst which is capable of catalyzing ester bond formation;

IV) optionally, removing the protecting group, and wherein the protecting group may comprise a functional group.

Step I) of the method provides a protected ascorbic acid by forming a protecting group from at least one hydroxy-functional group thereon. The protecting groups are the same as described above. In a specific embodiment the hydroxy Is are protected in the form of a trimethylsilyl (TMS) ether, and in a very specific embodiment the protected ascorbic acid comprises a tetra-O-trimethylsilyl ascorbic acid. Protection as a tetra-O-trimethylsilyl derivative allows enhanced miscibility of the ascorbic acid with the carboxy-functional organosiloxane. Protection as a tetra-O-trimethylsilyl derivative also allows the removal of the 6-O-TMS ether in situ through the action of the carboxy-functional siloxane, an additive such as a tertiary alcohol or water generated as a result of the esterification reaction. The latter also prevents the accumulation of water during the course of the reaction. Removal of the 6-O-TMS ether allows subsequent esterification of the 6-OH group of the otherwise protected ascorbic acid.

In this embodiment, ascorbic acid is reacted with 1,1,1,3,3,3-hexamethyldisilazane, typically in a suitable solvent like acetonitrile, as represented below.

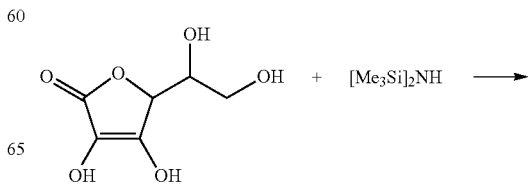

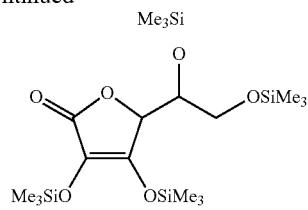

Step II) of the method involves mixing the protected ascorbic acid with a carboxy-functional organosiloxane having the formula $(R_3SiO)_nR_{(3-n)}Si-X-C(O)OR^1$ where R, n and X are the same as described above, and $R^1$ is a hydrocarbyl containing 1 to 20 carbon atoms or hydrogen, to form a solution. The carboxy-functional organosiloxane having the formula $(R_3SiO)_nR_{(3-n)}Si-X-C(O)OR^1$ may be prepared by any method known in the art. Typically, the carboxy-function organosiloxanes having the formula $(R_3SiO)_nR_{(3-n)}Si-X-C(O)OR^1$ are prepared by a hydrosilylation reaction between an organohydrogensiloxane of the average formula $(R_3SiO)_nR_{(3-n)}Si-H$, where R and n is as defined above, and a terminally aliphatic unsaturated carboxylic acid or ester. Techniques and catalysts for effecting hydrosilylation reactions are known in the art and any may be used to prepare the carboxy-functional organosiloxane useful in step II) of the present method. The terminally aliphatic unsaturated carboxylic acid or ester may have the formula $R^2-Y-R$ where $R^2$ is an monovalent unsaturated aliphatic hydrocarbon group, Y is a divalent hydrocarbon group, and $R^1$ is as defined above. Typically $R^2$ is $CH_2=CH-$, $CH_2=CHCH_2-$, or $CH\equiv C-$, and similar substituted unsaturated groups such as $H_2C=C(CH_3)-$, and $HC\equiv C(CH_3)-$. In one embodiment, the terminally aliphatic unsaturated carboxylic acid or ester is an undeconate ester, such as methyl 10-undecenoate or ethyl 10-undecenoate. A representative reaction scheme is shown below for producing a carboxy-functional organosiloxane useful in step II) of the method.

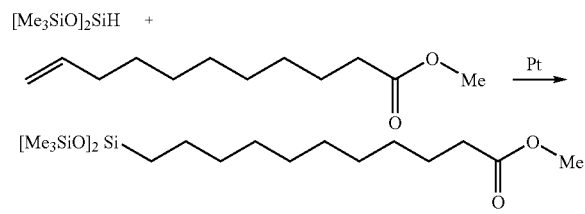

Step III) of the method involves contacting the solution with a biocatalyst which is capable of catalyzing ester bond formation. As used herein, the term "biocatalyst" includes: 1) natural, semi-synthetic, or metabolically engineered catalytic substances that are isolated from biological sources; and 2) synthetic catalytic molecules that mimic biological pathways. As used herein, the term "enzyme" includes proteins that are capable of catalyzing chemical changes in other substances. The enzymes can be wild-type enzymes or variant enzymes. Enzymes within the scope of the present invention include, but are not limited to, pullulanases, proteases, cellulases, amylases, isomerases, lipases, oxidases, oxidoreductases, hydrolases, aldolases, ketolases, glycosidases, oxidoreductases, hydrolases, aldolases, ketolases, glycosidases, lyases, ligases, transferases, and ligases.

As used herein, the term "lipolytic enzyme" refers to a polypeptide, protein or enzyme exhibiting a lipid degrading capability such as a capability of degrading a triglyceride or a phospholipid. A lipolytic enzyme may be, for example, a lipase, a phospholipase, an esterase or a cutinase. For the present invention, lipolytic activity may be determined according to any procedure known in the art. See, for example, Gupta et al, Biotechnol. Appl. Biochem. (2003) 37:63-71; Andre, Christophe, et al, U.S. Pat. No. 5,990,069 (International Publication WO 96/18729A1). As used herein, the term "protein" refers to polymers of large molecular mass composed of one or more polypeptide chains and whose monomers are amino acids joined together by peptide bonds. The terms "protein" and "polypeptide" are sometimes used interchangeably herein. The conventional one-letter or three-letter code for amino acid residues is used herein.

In a specific embodiment the biocatalyst comprises an enzyme, and in a more specific embodiment the biocatalyst comprises a hydrolase enzyme. In very specific embodiments the hydrolase enzyme is selected from the group consisting of a lipase, a protease, a phosphoesterase, an esterase, an amidase, a cutinase, and combinations thereof. In an even more specific embodiment the hydrolase enzyme comprises a lipase, and in a further specific embodiment the lipase comprises an immobilized form of *Candida antarctica* lipase B (CALB) marketed as N435 and available from Novozymes (Denmark).

Step III is typically performed under those conditions that favor the formation of ester bonds such as the removal or sequestration of water or low molecular weight alcohols to prevent the hydrolysis of the ester functionalities.

One of ordinary skill in the art will appreciate that additional synthetic methods could be used to produce the aforementioned compounds. For example, the linker group could be attached to ascorbic acid through ester bond formation, and subsequently the modified linker may be attached to an organosiloxane polymer comprising an appropriate chemistry. In one specific example, an ascorbic acid-modified linker bearing a terminal olefinic function could be attached to a hydride-functional organosiloxane via hydrosilylation. Alternatively, the ester linkage may result from the reaction of an organosiloxane containing an acid chloride, such as 10-undecenoyl chloride, with ascorbic acid.

The present disclosure further provides compositions containing the organosiloxane compounds as described above and a carrier fluid. The carrier fluid may be either an organic or silicone fluid. Suitable carrier fluids include silicones, both linear and cyclic, organic oils, organic solvents and mixtures of these. Specific examples of solvents may be found in U.S. Pat. No. 6,200,581, which is hereby incorporated by reference for this purpose.

Typically, the carrier fluid is a low viscosity silicone or a volatile methyl siloxane or a volatile ethyl siloxane or a volatile methyl ethyl siloxane having a viscosity at 25° C. in the range of 1 to 1,000 $mm^2$/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, hexamethyl-3,3,bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes.

Organic solvents may be exemplified by, but not limited to, aromatic hydrocarbons, aliphatic hydrocarbons, alcohols, aldehydes, ketones, amines, esters, ethers, glycols, glycol ethers, alkyl halides and aromatic halides. Hydrocarbons including isododecane, isohexadecane, Isopar L (C11-C13), Isopar H (C11-C12), hydrogenated polydecene. Ethers and esters including isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic carrier fluids suitable as a stand alone compound or as an ingredient to the carrier fluid include fats, oils, fatty acids, and fatty alcohols.

The amount of organosiloxane compounds combined with the carrier fluid may vary, such as from 0.1 wt % to 99 wt % percent of the organosiloxane in the carrier fluid.

Formulations containing organosiloxanes containing ester derivatives of ascorbic acid are contemplated for use in skin-lightening products. For example an emulsion of an organosiloxane containing ester derivatives of ascorbic acid and water containing 0.1 to 50% active ascorbic acid is applied to skin over a period of time to lighten the tone of the skin and remove blemishes and other discolorations. The active ascorbic acid in the said formulations can be that either covalently bound to carboxy-functional polysiloxanes, as well as free unconjugated ascorbic acid and mixtures thereof. Such formulations may optionally contain additional active compounds including vitamins, fragrances, anti-oxidants, herbal extracts, surfactants, humectants and the like.

One particular embodiment is directed to a keratinaceous tissue lightening agent comprising the inventive ester derivatives of either ascorbic acid. In a specific embodiment the keratinaceous tissue comprises human skin. A fun her embodiment provides a composition comprising a safe and effective amount of the keratinaceous tissue lightening agent and a suitable vehicle or base. In a more specific embodiment the composition is in the form of an emulsion. In one aspect of these embodiments, the novel compound comprises the inventive organosiloxanes containing ester derivatives of ascorbic acid and is contemplated as a controlled release keratinaceous tissue lightening agent.

A further embodiment provides a method of lightening keratinaceous tissue comprising topical application of the compositions comprising the inventive ester derivatives of ascorbic acid. One particular embodiment provides a method of lightening keratinaceous tissue comprising topical application of a controlled release composition which comprises the organosiloxanes containing ester derivatives of ascorbic acid. Such "controlled release," for example, may be achieved by delivery of a precursor which allows sustained release of ascorbic acid or undergoes subsequent conversion to free ascorbic acid. In a very specific embodiment the controlled release composition comprises inventive organosiloxanes containing ester derivatives of ascorbic acid.

Other embodiments are directed to personal care formulations comprising cosmetic or personal care compositions. Since the inventive organosiloxanes containing ester derivatives of ascorbic acid exhibit a relatively-higher permeability to the skin and mucosa, they are desirable for cosmetic applications which generally include skin, hair, and orally-usable products. The inventive ester derivatives may also be mixed with other cosmetically suitable ingredients such as oily bases, water-soluble bases, flavors, colors, dyes, refrigerants, humectanis, emollients, emulsifiers, gelation agents, viscosity enhancers, surfactants, stabilizers for foaming, clearances, antioxidants, germicides, putrefactive agents, coating-forming agents, and injection agents. The cosmetics according to the present invention contain at least 0.1 w/w %, and preferably at least 1.0 w/w % of the present inventive ester derivatives. It is also contemplated that the inventive ester derivatives may provide skin absorption enhancing effects to other benefit agents intended to provide benefit via absorption through the skin when administered in conjunction with those benefit agents. The inventive ester derivatives may also be desirably mixed with one or more pharmaceutical or nutritive agents such as vitamins, amino acids, peptides, hormones, extracts, vasodilators, blood circulation-promoting agents, cell-activating agents, anti-inflammatory drugs, urtication-preventing agents, skin-function-promoting agents, enzymes, and keratolyses. The mixtures may be in the form of liquid, emulsion, cream, paste, powder, granule, or solid products. The personal care compositions according to the present invention contain at least 0.1 w/w %, and preferably at least 1.0 w/w % of the present inventive ester derivatives.

Also contemplated are formulations with minimal water content where an organosiloxane containing ester derivative of ascorbic acid is formulated with additional polysiloxane materials including polydimethylsiloxane, polydimethylsiloxane polyethers, siloxane resins and other organosiloxane compounds. Such formulations may also contain additional active compounds including vitamins, fragrances, anti-oxidants, herbal extracts and the like.

EXAMPLES

These examples are intended to illustrate the invention to one of ordinary skill in the art and should not be interpreted as limiting the scope of the invention set forth in the claims. All measurements and experiments were conducted at 23° C., unless indicated otherwise.

Example 1

Preparation of Trisiloxane-undecyl Methyl Ester
Run 1A 1,1,1,3,5,5,5-Heptamethyltrisiloxane (1,329 g, 6.0 moles) and methyl 10-undecenoate (1,421.0 g, 7.2 moles) were placed in a 5000 mL three neck flask. The mixture was heated to 80° C. and 1.4 mL of a 1.0 weight percent chloroplatinic acid solution in 2-propanol was added (final platinum content is 4 ppm). The temperature of the mixture was then maintained at 100° C. for 24 hours. Measurement of the SiH content indicated that the reaction had proceeded to 98% completion. The excess methyl 10-undccenoate and other volatiles were removed by heating the mixture to 105° C./1 mmHg. Characterization of the product by FTIR, GC, $^{13}C$ NMR and $^{29}Si$ NMR indicated that the desired material was obtained as a slightly tan liquid.

Run 1B 1,1,1,3,5,5,5-Heptamethyltrisiloxane (1,208.2 g, 5.4 moles) was placed in a 5000 mL three neck flask. An addition funnel was charged with methyl 10-undecenoate (1,291.9 g, 6.5 moles). The content of the pot was heated to 75° C. and a small amount of methyl 10-undecenoate was introduced just prior to adding 0.45 mL of a 2.67 weight percent Pt IV solution (final Pt content of 4 ppm). The methyl 10-undecenoate was added from the addition funnel at a rate so the temperature of the reaction did not exceed 100° C. After the addition of the methyl 10-undecenoate was complete the mixture was maintained at 90° C. for 12 hours. The reaction was determined to be 98% complete based on the consumption of SiH. The crude reaction mixture was heated to 95° C./1 mmHg to remove volatiles and excess methyl 10-undecenoate from the product. Characterization of the product (GC, FTIR, $^{13}$C NMR and $^{29}$Si NMR) confirmed that the desired product had been obtained as a slightly tan liquid.

Run 1C 1,1,1,3,5,5,5-Heptamethyltrisiloxane (1,691.5 g, 7.6 moles) was placed in a 5000 mL three neck flask. An addition funnel was charged with methyl 10-undecenoate (1,000.1 g, 5.0 moles) which had been distilled at 71-74° C./1 mmHg prior to use. The content of the pot was heated to 70° C. and a small amount of methyl 10-undecenoate was introduced just prior to adding 0.60 mL of a 2.67 weight percent Pt IV solution (final Pt content of 4 ppm). The methyl 10-undecenoate was added from the addition funnel at a rate so the temperature of the reaction did not exceed 90° C. After the first amount of methyl 10-undecenoate had been added and additional 808.5 g (4.1 moles) was added via the addition funnel. After all the methyl 10-undecenoate had been added the mixture was maintained at 75° C. for 1 hour at which point FTIR indicated that 99.5% conversion had been achieved based on SiH consumption. Volatiles and excess methyl 10-undecenoate were removed from the crude product mixture by to 90° C./1 mmHg. The pressure in the reaction flask was brought to atmospheric and 50 g of activated carbon was introduced. The mixture was maintained at 90° C. for 6 hours. Next, the mixture was filtered through Celite to obtain the product as a colorless liquid. Characterization (GC, FTIR, $^{13}$C NMR and $^{29}$Si NMR) indicated that the desired product had been obtained. Additionally, ICP analysis indicated that the level of platinum in this product was <1 ppm.

Example 2

Preparation of Trisiloxane-undecyl Ethyl Ester 1,1,1,3,5,5,5-Heptamethyltrisiloxane (116.6 g, 0.52 moles) and ethyl 10-undecenoate (133.5 g, 0.63 moles) were placed in a 500 mL three neck flask. The mixture was heated to 80° C. and 60 µl of a 2.67 weight percent Pt IV solution (final Pt content of 5 ppm) was added. The temperature of the mixture was then maintained at 100° C. for 6 hours. Measurement of the SiH content indicated that the reaction had proceeded to 98.5% completion, The excess ethyl 10-undecenoate and other volatiles were removed by heating the mixture to 105° C./1 mmHg. Characterization of the product by FTIR, GC, $^{13}$C NMR and $^{29}$Si NMR indicated that the desired material was obtained as a slightly tan liquid.

Example 3

Preparation of Trimethylsilyl-functional Ascorbic Acid

Acetonitrile (1883.5 grams) was added into a 5000 mL three neck round bottom-jacketed flask. The flask was connected to a circulating water bath, containing an antifreeze/water solution, with a set point temperature of 0° C. A small vent was placed in the side neck of the flask. The flask was purged and then a Nitrogen sweep was applied throughout the reaction to remove any ammonia generated during the capping process. L-Ascorbic Acid (536.0 grams, 1.11 moles) was slowly added to the acetonitrile with rapid mixing using a mechanical stirrer with a Teflon stir rod and paddle. 1,1,1,3,3,3-Hexamethyldisilazane (1109.3 grams, 2.54 moles) was added to this mixture with rapid mixing. Mixing at 0° C. was maintained overnight. The mixture was then allowed to equilibrate to room temperature with mixing for two additional hours. The reaction mixture was transferred into single neck round bottom recovery flasks and concentrated under vacuum at 35-50° C. using a Rotavapor. A clear solution formed, which was poured into amber bottles, purged with nitrogen and placed into a 4° C. refrigerator for storage.

Example 4

Preparation of Ascorbyl Undecyl Trisiloxane (AUTS)

The trimethylsilyl-functional ascorbic acid of Example 3 (201.4 grams, 0.43 moles) and distilled-trisiloxane undecyl methyl ester of Example 1 (190.5 grams, 0.43 moles) were added into a 600 mL water-jacketed reaction flask that was connected to a circulating water bath with a set point temperature of 70° C. A nitrogen sweep was applied to the flask and a small vent was placed in one of the flask necks to remove any methanol formed during the reaction. A lipase enzyme immobilized on a polyacrylic resin bead (39.22 grams) and t-amyl alcohol (47.84 grams) were added to the flask with rapid mixing. The reaction mixture was mixed for 87.5 hours and then drained from the reactor into a 2000-milliliter single-neck round-bottom flask. Methanol (407.7 grams) was added to the flask, capped flask and mixed at room temperature for two hours on a Rotavapor without the use of vacuum. Filtered solid particles from the flask using a number five Whatman filter paper in a Buchner funnel with vacuum. Methanol was than stripped from the product under vacuum using a Rotavapor set to 65° C. until a viscous straw-colored fluid was remaining. Acetone (230.2 grams) was added to the reaction product and was mixed on a Rotavapor without the use of vacuum until the entire product was in a solution with the acetone. Solution was centrifuged at 3500 rpm to separate any unreacted ascorbic acid from the product. The liquid phase was recovered and centrifuged again. This process was repeated until there was no visually apparent residue present in the solution. The acetone was then removed by a vacuum strip on a Rotavapor at 68° C. Product was a clear, viscous, amber/straw-colored fluid.

Example 5

Preparation of Ascorbyl Undecyl Trisiloxane (from Ethyl Ester)

The trimethylsilyl-functional ascorbic acid of Example 3 (15.0 grams, 0.32 moles) and trisiloxane undecyl ethyl ester of Example 2 (13.6 grams, 0.32 moles) were added into a 50 mL water-jacketed reaction flask that was connected to a circulating water bath with a set point temperature of 70° C. A Nitrogen sweep was applied to the flask and a small vent was placed in one of the flask necks to remove any methanol formed during the reaction. A lipase enzyme immobilized on a polyacrylic resin bead (3.2 grams) and t-Amyl Alcohol (3.9 grams) was added to the flask with rapid mixing. The reaction mixture was mixed for 72 hours and then drained from the reactor into a 50-milliliter centrifuge tube. The tube was centrifuged at 4000 rpm to separate any un-reacted ascorbic acid from the product. The liquid phase was recovered and centrifuged again. This process was repeated until there was no visually apparent residue present in the solution. The capped product was a viscous, amber/straw-colored fluid.

Example 6

Preparation of Ascorbyl Undecyl Trisiloxane (AUTS) Using a Recycle Process

The trimethylsilyl-functional ascorbic acid of Example 3 (354.5 grams, 0.73 moles), trisiloxane undecyl methyl ester of Example 1 (320.9 grams, 0.73 moles) and cyclopentasiloxane (386.8 grams) were added into a 2000 mL water-jacketed reaction flask that was connected to a circulating water bath with a set point temperature of 70° C. A Nitrogen sweep was applied to the flask and a small vent was placed in one of the flask necks to remove any methanol formed during the reaction. The flask drain was plumbed using a glass adapter to attach ⅛ inch inside diameter Teflon tubing using compression fittings. The tubing was attached to the top of a one-inch diameter, water-jacketed column with a total length of 300 mL. The column was packed, from bottom to top, with a coarse disk filter, glass beads (35.0 grams) and a lipase enzyme immobilized on a polyacrylic resin bead (65.1 grams). Tubing was attached to the column outlet and run back to the original reaction flask. The reaction mixture was stirred slowly using a mechanical stirrer with a Teflon stir rod and paddle. This mixture was pumped from the flask bottom through tubing, pressure relief valve, pressure gauge, into the top of the column, through the bottom of the column and then pumped back into the flask. The reaction mixture was mixed/pumped for 124.5 hours and then drained from the reactor into a 3000-milliliter single-neck round-bottom flask. Methanol (684.7 grams) was added to the flask, capped flask and mixed at room temperature for two hours on a Rotavapor without the use of vacuum. Methanol was than stripped from the product under vacuum using a Rotavapor set to 65° C. until a viscous straw-colored fluid was remaining. Acetone (700.0 grams) was added to the reaction product and was mixed on a Rotavapor without the use of vacuum until the entire product was in a solution with the acetone. Solution was centrifuged at 3500 rpm to separate any unreacted ascorbic acid from the product. The liquid phase was recovered and centrifuged again. This process was repeated until there was no visually apparent residue present in the solution. The acetone was then removed by a vacuum strip on a Rotavapor at 68° C. Product was a clear, viscous, amber/straw-colored fluid.

Example 7

Thin Film Strip to Purify the Trimethyl Silyl Ether (TMS) Capped Ascorbyl Undecanoate Trisiloxane (AUTS) Product A reaction product mixture containing trimethylsilyl-functional ascorbic acid (such as from Example 3) was placed in the reservoir of a thin film stripping apparatus. The external jacket of the apparatus was heated to and maintained at 175±5° C. The vacuum was introduced to the system and allowed to run until the pressure in the system is below 1.5 mmHg. Once the temperature and pressure have reached the set values, the product mixture is introduced to the top of the thin film stripper wiper blades and the motor is now turned on to start the wiper assembly spinning. The material is introduced from the reservoir at such a rate as to not overwhelm the wiper blades (~1 ml/min). The volatile components under these conditions, the trimethyl silyl ether capped ascorbic acid and the methyl 10-undecanoate trisiloxane are volatilized and condense on the internal cold finger while the purified trimethyl silyl ether capped ascorbyl 10-undecanoate trisiloxane remains in the non-volatile portion of the thin film stripper. Both the non-volatile and volatile portions of the process are collected. Using this method, it is possible to obtain trimethyl silyl ether capped ascorbyl undecanoate trisiloxane that contains less than 1% of the trimethyl silyl ether capped ascorbic acid and less than 1% of the methyl 10-undecanoate trisiloxane.

Example 8

A Non-enzymatic Method to Prepare Ascorbyl 10-undecanote Trisiloxane

To a 50 ml three neck round bottom flask was added 5.0 g (28.4 mmoles) of ascorbic acid, 4.7 ml (3.4 g, 34.0 mmoles) of triethylamine and 30 ml of N,N,-dimethylformamide. To this mixture was slowly added, with stirring, 7.0 g (34.5 mmoles) of 10-undecenoyl chloride. During the addition, a slight exotherm was observed. The mixture was allowed to stir for 2.5 h and then filtered to remove the precipitate that had formed. The filtrate was diluted with toluene, placed in a separatory funnel and washed with 2×100 ml portions of water, 2×100 ml portions of saturated sodium bicarbonate, 2×100 ml portions of water and then 1×100 ml portion of saturated sodium chloride. The organic layer was dried over anhydrous magnesium sulfate, filtered and the solvent removed on a rotary evaporator to yield a slightly yellow oil.

Example 9

Skin Lightening with Ascorbyl Undecyl Trisiloxane (AUTS)

This example illustrates cell viability properties and efficacy of skin lightening formulations according to the present invention. In particular, two formulations according to the present invention (containing AUTS as prepared according to Example 4), water (a negative control), 1% kojic acid (Sigma, Wis.) in water (positive control), and ascorbyl tetraisopalmitate in D5 (decamethylcyclopentasiloxane) were assayed and compared for cell viability and skin lightening efficacy (see Table 1)

TABLE 1

| Preparations assayed and cell viability by MTT | | | | |
|---|---|---|---|---|
| Compound | Carrier | Concentration[1] | Dosed | Viability by MTT |
| AUTS | D5 | 3.2% | 10 μL | 95.5% |
| AUTS | D5 | 3.2% | 25 μL | 96.5% |
| VC-IP | D5 | 6.4% | 10 μL | 94.1% |
| VC-IP | D5 | 6.4% | 25 μL | 98.2% |

Negative control: 25 μL water
Positive control: 25 μL kojic acid, 1%
Test Preparation: 3.2 wt % AUTS in decamethylcyclopentasiloxane (D5).
Reference Preparation: 6.4% Nikkol VC-IP (ascorbyl tetraisopalmitate supplied by Nikko Chemicals Co., Ltd. Of Japan (in D5)
[1]The concentrations of the test material and the reference material were set to provide the equivalent of 1% ascorbic acid in the test solutions.

MELANODERM™ cell viability was tested by MTT assay after exposure to test and reference preparations. The assays were carried out using Melanoderm tissue model MEL 300 A cell line (MELANODERM tissue model available from MatTek, Ashland, Mass.), This melanoderm model consists of normal, human-derived epidermal keratinocytes and melanocytes that have been co-cultured to form a multilayer, highly differentiated model of human epidermis. MTT data showed that viability of MelanoDerm skin model was not affected by the treatment. (Cell viability with both materials in D5 at 10 and 25 μL dose was >90%).

Skin whitening effect was evaluated by measuring melanin concentration (μg/ml) after six applications of each preparation. The results are summarized in Table 2.

TABLE 2

Melanin concentration at Day 10 Test Preparation vs Reference Preparation

|  | AUTS, 10 μl | VC-IP, 10 μl | AUTS, 25 μl | VC-IP, 25 μl | Kojic Acid*** 25 μL |
|---|---|---|---|---|---|
| Average (μg/ml) | 37.4* | 57.8* | 26.6** | 55.2** | 41.9 |
| SD | 7.5 | 3.8 | 4.4 | 5.9 |  |
| P value | 1.1E−03 |  | 7.3E−05 |  |  |

*Significantly lower melanin concentration (p < 0.05) in cell culture dosed with AUTS, 10 μl in comparison with VC-IP, 10 μl.
**Significantly lower melanin concentration (p < 0.05) in cell culture dosed with AUTS, 25 μl in comparison with VC-IP, 25 μl.
***1 wt % in water

Example 9 (Comparative)

Solubility of Ascorbyl Undecyl Trisiloxane (AUTS) in Various Personal Care Solvents The solubility characteristics of the organosiloxanes containing ester derivatives of ascorbic acid of the present disclosure vs the organosiloxanes as taught in WO2006/066227 is shown in this representative comparative example.

A 36 wt % mixture of the referenced sample and listed solvents were prepared in a glass vial. The sealed glass vials containing the mixtures were then placed in a 60° C. water bath and periodically shaken and observed. The results, as summarized in Table 3, show the representative organosiloxanes of the present disclosure had improved solubility characteristics.

Comparative sample #1 is the same average formula as the ascorbyl containing organosiloxane of Example 4 in WO2006/066227.

Comparative sample #2 is the same average formula as the ascorbyl containing organosiloxane of Example 6 in WO2006/066227.

AUTS is representative of Example 4 as described above.

TABLE 3

|  | Reference | A | B | C | D | E | Water |
|---|---|---|---|---|---|---|---|
| Bis-Ascorbyl Undecyl Tetramethyldisiloxane | Comparative sample #1 | No | No | No | No | na | Yes* |
| Bis-Ascorbyl Undecyl Polydimethylsiloxane | Comparative sample #2 | Yes | No | No | Yes | Yes | No |
| Ascorbyl Undecyl | AUTS | Yes** | Yes** | Yes** | na | Yes** | No |

A = C12-15 Alkyl Benzoate (FINSOLV TN)

B = Cyclopentasiloxane (Dow/Corning 245 Fluid)

C = Squalane (Uniqema PRIPURE 3759)

D = Tricaprylin (TRIVENT OC-G)

E = Caprylic/Capric Triglyceride

*forms a translucent mixture that thickens to a viscous hazy liquid when cooled

**dissolves to form a solution that ranges from nearly clear to hazy, depending on the solvent; solutions gel when cooled to room temperature

Example 10

Personal Care Formulations Containing Ascorbyl Undecyl Trisiloxane (AUTS)

Representative ascorbyl undecyl trisiloxanes were incorporated into various personal care formulations as illustrated below to demonstrate.

Facial Moisturizer

| Weight % | INCI name | Trade Name (Supplier) |
|---|---|---|
| Part A |  |  |
| 5.0% | Hydroxyethylacrylate/Sodium Acryloyldimethyl Taurate Copolymer (and) Isohexadecane (and) Polysorbate 80 | Simulgel FL (SEPPIC) |
| 6.8% | Cyclopentasiloxane | DowCorning ® 245 Fluid (DOW CORNING) |
| 3.2% | Ascorbyl Undecyl Trisiloxane (AUTS) |  |
| 4.0% | Diethylhexyl Succinate | Crodamol OSU (CRODA) |
| Part B |  |  |
| 2.0% | Glycerin |  |
| 78.8% | Deionized Water |  |
| 0.2% | Propylene Glycol (and) Diazolidinyl Urea (and) Iodopropynyl Carbamate | Liquid Germall Plus (SUTTON LABS) |
| 100.0% |  |  |

PROCEDURE: Combine the AUTS, cyclopentasiloxane, and diethylhexyl succinate in a vessel that is large enough to hold the entire batch. Heat these ingredients with gently mixing to about 60° C. until the AUTS disperses completely. Add the Simulgel FL and mix until uniform while maintaining the temperature at about 55° C. Mix the ingredients for Part B in a separate vessel until a homogenous solution is obtained and heat to about 55° C. Slowly add Part B to Part A with continuous mixing. The batch will thicken as more of Part B is added. After all of Part B has been added, mix the batch with sufficient agitation to achieve good turnover and allow the batch to cool to room temperature.

Facial Moisturizer with Inorganic Sunscreen

| Weight % | INCI name | Trade Name (Supplier) |
|---|---|---|
| Part A | | |
| 5.0% | Hydroxyethylacrylate/Sodium Acryloyldimethyl Taurate Copolymer (and) Isohexadecane (and) Polysorbate 80 | Simulgel FL (SEPPIC) |
| 6.8% | Cyclopentasiloxane | DowCorning ® 245 Fluid (DOW CORNING) |
| 3.2% | Ascorbyl Undecyl Trisiloxane (AUTS) | |
| 4.0% | Titanium Dioxide (and) Alumina (and) Dimethicone | UV-TITAN M262 (Kemira) |
| 6.0% | Dimethicone | DowCorning ® 200 Fluid/100 cSt (DOW CORNING) |
| Part B | | |
| 2.0% | Glycerin | |
| 78.8% | Deionized Water | |
| 0.2% | Propylene Glycol (and) Diazolidinyl Urea (and) Iodopropynyl Carbamate | Liquid Germall Plus (SUTTON LABS) |
| 100.0% | | |

PROCEDURE: Disperse the UV-TITAN M262 in the dimethicone using high shear mixing equipment to fully disperse the titanium dioxide. Set this dispersion aside. Combine the AUTS and cyclopentasiloxane in a vessel that is large enough to hold the entire batch. Heat these ingredients with gently mixing to about 60° C. until the AUTS disperses completely. Add the Simulgel FL and the titanium dioxide dispersion, then mix until uniform while maintaining the temperature at about 55° C. Mix the ingredients for Part B in a separate vessel until a homogenous solution is obtained and heat to about 55° C. Slowly add Part B to Part A with, continuous mixing. The batch will thicken as more of Part B is added. After all of Part B has been added, mix the batch with sufficient agitation to achieve good turnover and allow the batch to cool to room temperature.

Facial Moisturizer with Organic Sunscreen

| Weight % | INCI name | Trade Name (Supplier) |
|---|---|---|
| Part A | | |
| 7.5% | Hydroxyethylacrylate/Sodium Acryloyldimethyl Taurate Copolymer (and) Isohexadecane (and) Polysorbate 80 | Simulgel FL (SEPPIC) |
| 6.8% | Cyclopentasiloxane | DowCorning ® 245 Fluid (DOW CORNING) |
| 3.2% | Ascorbyl Undecyl Trisiloxane (AUTS) | |
| 7.5% | Ethylhexyl Methoxycinnamate (Octinoxate) | Escalol 557 (International Specialty Products) |
| Part B | | |
| 2.0% | Glycerin | |
| 72.8% | Deionized Water | |
| 0.2% | Propylene Glycol (and) Diazolidinyl Urea (and) Iodopropynyl Carbamate | Liquid Germall Plus (SUTTON LABS) |
| 100.0% | | |

PROCEDURE: Combine the AUTS, cyclopentasiloxane, and ethylhexyl methoxycinnamate in a vessel that is large enough to hold the entire batch. Pleat these ingredients with gently mixing to about 60° C. until the AUTS disperses completely. Add the Simulgel FL and mix until uniform while maintaining the temperature at about 55° C. Mix the ingredients for Part B in a separate vessel until a homogenous solution is obtained and heat to about 55° C. Slowly add Part B to Part A with continuous mixing. The batch will thicken as more of Part B is added. After all of Part B has been added, mix the batch with sufficient agitation to achieve good turnover and allow the batch to cool to room temperature.

Anhydrous Sunscreen Ointment

| Wt. % | INCI name | Trade Name (Supplier) |
|---|---|---|
| 2.0% | Titanium Dioxide (and) Alumina (and) Dimethicone | UV-TITAN M262 (Kemira) |
| 3.0% | Dimethicone | Dow Corning ® 200 Fluid/100 cSt (DOW CORNING) |
| 21.8% | Cyclopentasiloxane | Dow Corning ® 245 Fluid (DOW CORNING) |
| 65.0% | Cyclopentasiloxane (and) Dimethicone Crosspolymer | Dow Corning ® 9045 Silicone Elastomer Blend (DOW CORNING) |
| 3.2% | Ascorbyl Undecyl Trisiloxane (AUTS) | |
| 5.0% | Ethylhexyl Methoxycinnamate (Octoxinate) | |
| 100.0% | | |

PROCEDURE: Disperse the UV-TITAN M262 in the dimethicone using high shear mixing equipment to fully disperse the titanium dioxide. Combine the remaining ingredients in a suitable mixing vessel. Heat these ingredients to about 60° C. and then mix until the AUTS is melted and uniformly dispersed. Begin cooling the batch and add the titanium dioxide/dimethicone dispersion to the batch. Mix until uniform and continue mixing until the batch cools to room temperature.

Water-in-Oil Sunscreen Lotion

| Weight % | INCI name | Trade Name (Supplier) |
|---|---|---|
| Part A | | |
| 3.4% | Titanium Dioxide (and) Alumina (and) Dimethicone | UV-TITAN M262 (Kemira) |
| 6.6% | Dimethicone | Dow Corning ® 200 Fluid/100 cSt (DOW CORNING) |
| 7.5% | Cyclopentasiloxane (and) PEG/PPG-18/18 Dimethicone | Dow Corning ® 5225C Formulation Aid (DOW CORNING) |
| 3.2% | Ascorbyl Undecyl Trisiloxane (AUTS) | |
| 6.8% | Cyclopentasiloxane | Dow Corning ® 245 Fluid (DOW CORNING) |
| 5.0% | Aluminum Starch Octenyl Succinate | Dry Flo PC/National Starch and Chemical |
| 4.0% | Cyclopentasiloxane (and) Trimethylsiloxysilicate | Dow Corning ® 749 Fluid (DOW CORNING) |
| Part B | | |
| 62.3% | Water | |
| 1.0% | Sodium Chloride | |
| 0.2% | Polysorbate 20 | Tween 20 (CRODA) |
| 100.0% | | |

PROCEDURE: Disperse the UV-TITAN M262 in the dimethicone using high shear mixing equipment, to fully disperse the titanium dioxide. Combine the titanium dioxide dispersion with the remaining ingredients for Part A in a mixing vessel that is large enough to contain the entire batch. Heat Part A to about 60° C. and mix until the AUTS is melted and uniformly dispersed. Combine the ingredients for Part B in a separate vessel and mix until a homogeneous solution is obtained, then heat to about 60° C. Slowly add Part B to Part A while mixing vigorously to produce a turbulent mixing action such that Part B is quickly incorporated into the batch as it is added, When all of Part B has been added, begin cooling and continue mixing for another 10-15 minutes.

The invention claimed is:

1. A compound having the formula;

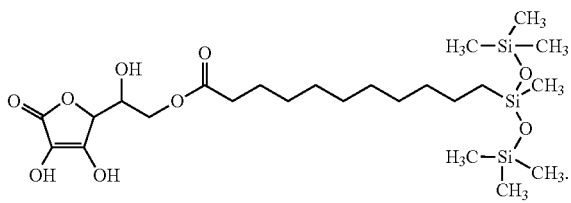

2. A composition comprising the compound according to claim 1 and a carrier fluid.

3. The composition of claim 2 wherein the carrier fluid is selected from an organic or silicone fluid.

4. The composition of claim 3 wherein the carrier fluid is a volatile silicone.

5. The composition of claim 4 wherein the volatile silicone is an organocyclopolysiloxane.

6. The composition of claim 5 wherein the organocyclopolysiloxane is decamethylcyclopentasiloxane.

7. A keratinaceous tissue lightening agent composition comprising the compound as claimed in claim 1.

8. The keratinaceous tissue lightening agent composition of claim 7 wherein the keratinaceous tissue comprises human skin.

9. The keratinaceous tissue lightening agent composition of claim 8 further comprising a suitable vehicle or base.

10. The keratinaceous tissue lightening agent composition of claim 9 further comprising free ascorbic acid.

11. The keratinaceous tissue lightening agent composition of claim 9 wherein the composition is in the form of an emulsion.

12. A process for lightening keratinaceous tissue comprising topically applying the compound of claim 1.

13. A personal care composition comprising the compound of claims 1.

14. The personal care composition of claim 13 wherein the personal care composition is a moisturizer, suncare, or cosmetic formulation.

* * * * *